United States Patent
Ciulla et al.

(10) Patent No.: US 10,245,052 B2
(45) Date of Patent: Apr. 2, 2019

(54) SYSTEMS, DEVICES, AND METHODS FOR TISSUE EXTRACTION

(71) Applicant: Boston Scientific Scimed, Inc., Maple Grove, MN (US)

(72) Inventors: Ronald Ciulla, Westford, MA (US); Kenneth J. Daignault, Holden, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 895 days.

(21) Appl. No.: 14/554,610

(22) Filed: Nov. 26, 2014

(65) Prior Publication Data

US 2015/0148597 A1 May 28, 2015

Related U.S. Application Data

(60) Provisional application No. 61/909,568, filed on Nov. 27, 2013.

(51) Int. Cl.
| | |
|---|---|
| *A61B 17/22* | (2006.01) |
| *A61B 17/221* | (2006.01) |
| *A61B 1/307* | (2006.01) |
| *A61B 1/05* | (2006.01) |
| *A61B 90/00* | (2016.01) |

(Continued)

(52) U.S. Cl.
CPC .......... *A61B 17/22031* (2013.01); *A61B 1/05* (2013.01); *A61B 1/307* (2013.01); *A61B 17/221* (2013.01); *A61B 18/22* (2013.01); *A61B 90/30* (2016.02); *A61B 90/37* (2016.02); *A61B 2017/00274* (2013.01); *A61B 2017/00858* (2013.01); *A61B 2017/2212* (2013.01); *A61B 2017/2215* (2013.01); *A61B 2018/00547* (2013.01); *A61B 2018/00601* (2013.01); *A61B 2018/00982* (2013.01)

(58) Field of Classification Search
CPC .................. A61B 1/307; A61B 17/221; A61B 2017/2212; A61B 2017/2215; A61B 2017/2217; A61B 2018/00982; A61B 1/00135; A61B 1/042; A61B 17/29; A61B 2017/2926; A61B 1/018; A61B 18/1445
USPC .................................. 600/565; 606/114, 115
See application file for complete search history.

(56) References Cited

U.S. PATENT DOCUMENTS 4,475,539 A * 10/1984 Konomura ............. A61B 1/042
  348/68
4,567,880 A * 2/1986 Goodman .......... A61B 1/00068
  600/135

(Continued)

OTHER PUBLICATIONS

Boston Scientific Corporation, ZeroTip™ Nitinol Stone Retrieval Basket (brochure), 2009 (2 pages).

*Primary Examiner* — Timothy J Neal
*Assistant Examiner* — Aaron B Fairchild
(74) *Attorney, Agent, or Firm* — Bookoff McAndrews, PLLC (57) ABSTRACT

Medical devices, systems, and related methods of use are disclosed. The systems may comprise a sheath for insertion into a body lumen and an extraction tool for passage through the sheath, wherein the extraction tool may include a handle, an end effector, and an optical device. Methods disclosed herein include introducing an extraction tool into a urethra for retrieving and removing tissue from the body, e.g., with an end effector, without morcellating the excised tissue.

19 Claims, 3 Drawing Sheets

(51) Int. Cl.
*A61B 90/30* (2016.01)
*A61B 17/00* (2006.01)
*A61B 18/00* (2006.01)
*A61B 18/22* (2006.01)

(56) References Cited

U.S. PATENT DOCUMENTS

| | | | | |
|---|---|---|---|---|
| 5,762,458 | A * | 6/1998 | Wang | A61B 17/11 |
| | | | | 414/1 |
| 7,491,210 | B2 * | 2/2009 | Dubrul | A61B 17/221 |
| | | | | 606/114 |
| 7,727,227 | B2 | 6/2010 | Teague et al. | |
| 2002/0120277 | A1 * | 8/2002 | Hauschild | A61B 17/221 |
| | | | | 606/108 |
| 2003/0229263 | A1 * | 12/2003 | Connors | A61B 1/307 |
| | | | | 600/29 |
| 2005/0059890 | A1 * | 3/2005 | Deal | A61B 1/018 |
| | | | | 600/433 |
| 2005/0261706 | A1 * | 11/2005 | Cheng | A61B 17/22 |
| | | | | 606/113 |
| 2008/0058836 | A1 * | 3/2008 | Moll | A61B 17/221 |
| | | | | 606/130 |
| 2008/0167526 | A1 * | 7/2008 | Crank | A61B 1/307 |
| | | | | 600/135 |

\* cited by examiner

SYSTEMS, DEVICES, AND METHODS FOR TISSUE EXTRACTION

CROSS-REFERENCE TO RELATED APPLICATIONS

This application claims the benefit of priority from U.S. Provisional Application No. 61/909,568, filed on Nov. 27, 2013, the entirety of which is incorporated by reference herein.

TECHNICAL FIELD

The present disclosure generally relates to system, devices, and methods for extracting tissue.

BACKGROUND

Benign Prostatic Hyperplasia (BPH) is a condition of a non-cancerous enlargement of the prostate gland, especially prevalent in older men. As the prostate becomes enlarged, it may put pressure on the urethra and may cause pain, difficulty in urination, and infection. Holmium Laser Enucleation of the Prostate (HoLEP) is a technique for treating BPH. HoLEP generally uses a laser device that is inserted into the urethra, e.g., through a sheath, to target and remove prostate tissue. The laser device is used to cut excess prostate tissue to relieve pressure on the urethra. During the procedure, pieces of the excised tissue are moved into the bladder for removal from the body with a morcellator. The morcellator is a surgical device having a small opening at its distal end equipped with one or more blades and suction capability. The morcellator uses suction to draw the tissue to the opening, wherein the blades cut the tissue into sufficiently small pieces for removal via a narrow return conduit of the morcellator.

Due to its narrow return conduit and small opening, the morcellator often requires a significant amount of time for tissue removal. Other complications associated with the morcellator include drawing the tissue to the opening, since the tissue generally moves throughout the bladder and pieces of tissue have a tendency to bounce off or be deflected from the morcellator. Moreover, the morcellator has moving blades and may pose a risk of damaging the bladder, e.g., a mucosal lining of the bladder. Setting up the number of components used in the morcellator procedure may also require additional time. Thus, it may be desirable to provide for alternative systems and methods for tissue extraction.

BRIEF SUMMARY

In at least one embodiment, a method of removing tissue from a body is disclosed. The method may include introducing an extraction tool into urethra, wherein the extraction tool may extend between a proximal end and a distal end, wherein the distal end may include an end effector, the extraction tool having a channel greater than about 20 Fr; grasping the tissue with the end effector; and, without morcellating the tissue, removing the extraction tool with the tissue from the body.

The method may include one or more following: the extraction tool may include an optical device, the method further comprising viewing the tissue with the optical device; the optical device may include an eyepiece operably connected to a remote imaging system and/or an electronic camera; grasping the tissue may include deploying the end effector from a collapsed state into an expanded state, and grasping the tissue with the end effector in the expanded state; the end effector may be self-expanding; the extraction tool may include a handle and deploying the end effector from the collapsed state into the expanded state may include operating a control mechanism in the handle; the end effector may include a modified surface for grasping the tissue; securing the tissue with the end effector after grasping; the tissue may include prostate tissue; the tissue may include loose tissue located in a bladder; the method may comprise introducing a sheath into the urethra, and then introducing the extraction tool into the sheath; pulling the extraction tool proximally through the sheath for removal may secure the tissue within the extraction tool; the sheath may include an inlet for introducing a fluid into the sheath, e.g., for entry into the bladder; the method may comprise introducing a saline solution into the sheath through the inlet; or the channel may be greater than about 26 Fr.

Embodiments of the present disclosure also include a method of performing holmium laser enucelation of the prostate, the method comprising excising prostate tissue with a laser apparatus; moving the excised tissue into a bladder; introducing an extraction tool into a urethra and advancing the extraction tool toward the bladder, wherein the extraction tool may extend between a proximal end and a distal end, and wherein the distal end may include an end effector, the extraction tool having a channel greater than about 26 Fr; grasping the excised tissue with the end effector; and removing the extraction tool with the excised tissue from the body.

The method may include one or more following: the extraction tool may include an optical device, the method further comprising viewing the excised tissue with the optical device; grasping the excised tissue may include deploying the end effector from a collapsed state into an expanded state, and grasping the excised tissue with the end effector when in the expanded state; or the channel may be between about 26 Fr and about 27 Fr.

Embodiments of the present disclosure also include a system for removing tissue from a body, the system comprising: a sheath configured for introduction into a urethra; and an extraction tool for passage through the sheath, wherein the extraction tool extends between a proximal end and a distal end and includes: an optical device at the distal end, the optical device operably coupled to a remote imaging system; an end effector at the distal end, the end effector including a collapsed state and an expanded state and including a modified surface for grasping and securing the tissue; and a handle at the proximal end, wherein the handle may include a control mechanism for deploying the end effector; wherein the extraction tool may have a channel greater than about 26 Fr.

BRIEF DESCRIPTION OF THE DRAWINGS

Embodiments of the present invention are described with reference to the following drawings for exemplary purposes only. In the drawings, like reference numerals refer to like parts throughout the various figures unless otherwise specified.

For a better understanding of the presently disclosed subject matter, reference will be made to the following Detailed Description, which is to be read in association with the accompanying drawings, wherein.

DETAILED DESCRIPTION

Embodiments of the present disclosure include a medical device for capturing, removing, and/or retrieving a material from a body, and methods of use thereof. In some embodiments, the medical device may be used to retrieve tissue, e.g., loose or unattached tissue that has been cut away or otherwise severed or freed from attachment to the body. In at least one embodiment, the tissue to be removed may include prostate tissue.

For convenience, the medical device discussed here is generally referred to as an extraction tool/device, however, this reference is merely made for convenience, and is intended to include devices capable of other or additional operations and/or functions. In the following sections, embodiments of the present disclosure will be described using the bladder as an exemplary body organ. It will be understood that the bladder is merely an example and that the device may be used in other suitable organs.

Figure 1:
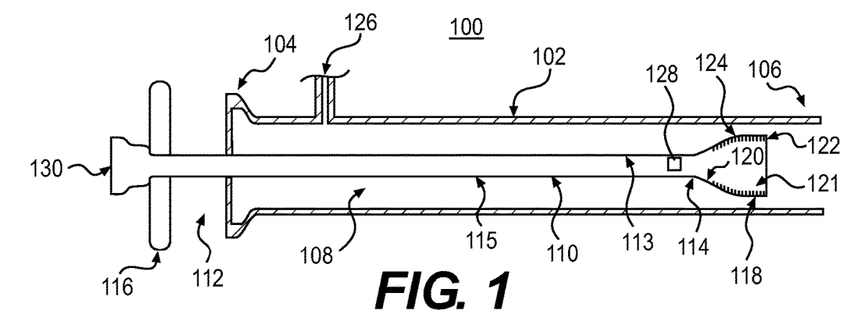
FIG. 1 is a schematic view of an exemplary system including an extraction tool, in accordance with an embodiment of the present disclosure.

FIG. 1 is a schematic view of an exemplary medical device 100 including an extraction tool 110. The medical device 100 may also include a sheath 102 through which the extraction tool 110 may pass. The sheath 102 may include any appropriate structure configured to be inserted and manipulated within a cavity of a patient's body such as, e.g., a catheter or endoscope. In some embodiments, the sheath 102 may have a substantially circular cross-sectional shape. Other suitable cross-sectional shapes such as elliptical, oval, or polygonal may also be used.

The sheath 102 may include a proximal end 104, a distal end 106, and at least one channel 108 extending between the proximal end 104 and the distal end 106. The channel 108 may extend along a longitudinal axis of the medical device 100 such as a central axis of the sheath 102. The channel 108 may extend through at least a portion of the sheath 102, or the entire length of the sheath 102. The channel 108 of the sheath 102 may include a suitable coating, e.g., a hydrophilic coating, to facilitate insertion and/or removal of the extraction tool 110. As shown in FIG. 1, the sheath 102 may include a single channel 108, but it is understood that the sheath 102 may include multiple channels through which an operator may introduce one or more medical devices. For example, during a HoLEP procedure, a surgeon or other operator may introduce a laser apparatus into one channel and a device such as, e.g., a light source, a camera, or other device or tool into other channels as and when required.

The sheath 102 may include one or more inlets 126. In some embodiments, the inlet(s) 126 may be used to deliver a fluid such as water or a saline solution to a target location within the body. For example, a fluid may be introduced into the bladder to help protect the tissue wall or mucosal lining of the bladder, e.g., from damage during a medical procedure. The inlet 126 may be in fluid communication with the channel 108 of the sheath 102 such that fluid may travel the length of the channel 108, e.g., into the bladder to at least partially inflate the bladder. The inlet 126 may be connected to an external fluid system or reservoir (not shown) for delivering or injecting the fluid. The external fluid system may be coupled to the sheath 102, e.g., at the proximal end 104 of the sheath 102. The number of inlets 126 may correspond to the number of channels 108 within the sheath 102. Alternatively, the number of inlets 126 may be greater or fewer than the number of channels 108 within the sheath 102. In some embodiments, the inlet(s) 126 may include one or more connectors to couple the sheath 102 to one or more other device(s), for example via a luer lock connector or Tuohy Borst connector.

The sheath 102 may be of any suitable size for receiving the extraction tool 110. For example, the sheath 102 may include an opening and/or working channel 108 sufficiently large to facilitate removal of tissue of various sizes, including relatively larger pieces of tissue, with the extraction tool 110, without further cutting the tissue into smaller pieces, such as with a morcellator. The extraction tool 110 may be introduced into the body, e.g., into the urethra, through the channel 108 of the sheath 102. In some embodiments, the extraction tool 110 may be configured to be steerable independently of the sheath 102 using a suitable control mechanism.

The extraction tool 110 may include a proximal end 112, a distal end 114, and an outer surface 115. The extraction tool 110 may include a channel 113 or lumen extending between the proximal end 112 and the distal end 114. The channel 113 may run through the entire length of the extraction tool 110 and may be configured to receive one or more medical devices such as an optical device 128 or other device. In some embodiments, the extraction tool 110 may include more than one channel 113 and/or corresponding openings for a variety of purposes such as inserting additional medical devices.

The extraction tool 110 may have a channel 113 of a suitable size or dimensions to facilitate tissue removal without morcellating or otherwise cutting the tissue into smaller pieces. A larger sized working channel 113 may allow for faster, more efficient, and/or more convenient removal of excised tissue from the body in comparison to devices having a narrow working channel, such as a morcellator. For example, the channel 113 of the extraction tool 110 may be greater than the diameter of a standard Nephroscope working channel, e.g., greater than about 15 Fr, greater than about 20 Fr, greater than about 25 Fr, or greater than about 26 Fr. In some embodiments, the channel may range from about 20 Fr to about 30 Fr, from about 25 Fr to about 30 Fr, or from about 26 Fr to about 27 Fr. In at least one embodiment, the channel 113 of the extraction tool 110 may be about 25 Fr, about 26 Fr, about 27 Fr, or about 28 Fr. The sheath 102 may have any other suitable dimensions that are beneficial or otherwise useful according to the needs and preferences of an operator and/or patient.

In some embodiments, the extraction tool 110 may have a substantially circular cross-section. In other embodiments, the extraction tool 110 have other suitable cross-sectional shapes including, but not limited to, square, rectangular, triangular, or oval, for example. The cross-sectional shape of the extraction tool 110 may be uniform or may vary along its length. Additionally, the cross-sectional shape of the extraction tool 110 may vary based on the cross-sectional shape of the sheath 102.

The extraction tool 110 may comprise one or more flexible materials, e.g., at least a portion of the extraction tool 110 may have a flexible or a semi-flexible structure. The extraction tool 110 may be flexible along its entire length or along at least a portion of its length. In some embodiments, the distal end 114 of the extraction tool 110 may be flexible while the proximal end 112 may be rigid. Flexibility may help the extraction tool 110 maneuver turns in body lumens and/or deflect in the desired direction, while rigidity may provide the necessary force to push the extraction tool 110 forward.

The extraction tool 110 may include one or more of an optical device 128, an end effector 118, and/or a handle 116. In some embodiments, for example, the extraction tool 110 may include one or more optical devices 128, e.g., to allow an operator to visualize material within the body, such as tissue for removal from the body. The optical device 128 may include one or more components, e.g., eyepiece 130 or other component such as, e.g., a telescope, a electronic camera, or fiber optic cable. In some embodiments, the optical device 128 may be connected to a remote imaging system for analyzing, displaying, and/or recording images collected by the optical device 128. The extraction tool 110 and/or the optical device 128 may be configured for use with existing telescope technologies. In some embodiments, the extraction tool 110 may be configured for single use (e.g., disposable), while the optical device 128 may be re-usable.

One or more components of an optical device 128 may be provided at the proximal end 112 of the tool 110, e.g., coupled to the handle 116. Additionally, one or more components of an optical device 128 may be coupled to the distal end 114 of the extraction tool 110. For example, the extraction tool 110 may include an optical device 128 disposed within the channel 113 of the extraction tool 110, such as near the end effector 118 for viewing features within the body and/or material for capture by the end effector 118. In some embodiments, the extraction tool 110 may include an optical device 128 coupled to the distal end 114 of the extraction tool 110, e.g., outside of the end effector 118, wherein the optical device 128 is configured for viewing features within the body or material for capture by the end effector 118. The optical device 128 may be integrated into the extraction tool 110. A suitable light source may be utilized for providing illumination to visualize a target location via the optical device 128, e.g., xenon light, LEDs, or other suitable light sources.

The end effector 118 may comprise a separate element that is temporarily or permanently coupled to the extraction tool 110, e.g., via molding, snap fit, screw fit, gluing, welding, or other suitable mechanism depending on the material from which the end effector 118 is made or otherwise formed. In some embodiments, the end effector 118 may be integrally formed with the extraction tool 110. The end effector 118 may be made of any suitable biocompatible material(s), including, but not limited to, one or more polymers such as plastics or silicone, cloth or fiber, metals such as shape memory alloys, or combinations thereof.

The end effector 118 may have a proximal end, a distal end 122, an inner surface 120, and an outer surface 124. The end effector 118 may be modified, such as to include a surface feature to facilitate capture of a material, e.g., increase a frictional force or gripping capability of the end effector 118 upon contact with tissue. For example, the inner surface 120 may including a coating or be textured 121 for better gripping of the tissue and to help in securing the tissue during removal. In some embodiments, the end effector 118 may assist in compressing the tissue for removal. The outer surface 124 of the end effector 118 may include a hydrophilic material or coating to facilitate insertion and/or removal of the extraction tool 110 from the sheath 102. The end effector 118 may have any suitable configuration for grasping or otherwise capturing a material and/or securing the material.

In some embodiments, the end effector 118 may be self-expandable. In other embodiments, the end effector 118 may be configured to expand by a proximal control mechanism, e.g., incorporated in the handle 116 of the extraction tool 110.

Figure 2A:
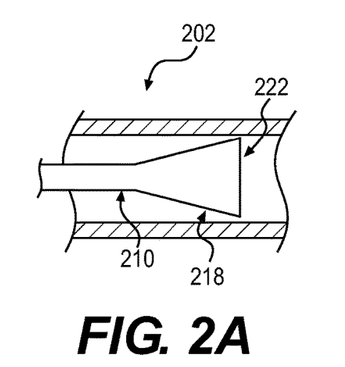
FIGS. 2A and 2B illustrate collapsed and expanded configurations, respectively, of an end effector.
Figure 2B:
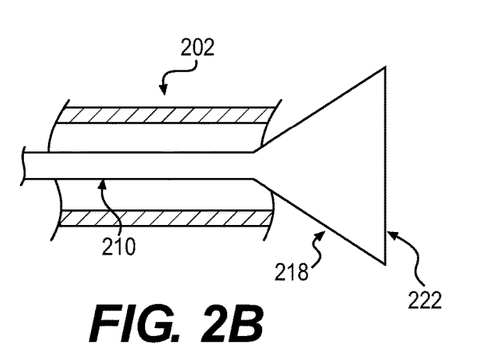

FIGS. 2A and 2B illustrate an exemplary self-expandable end effector 218 of an extraction tool 210, which may be substantially similar to end effector 118 and extraction tool 110 of FIG. 1 and include any of the features associated with extraction tool 110. During operation, the end effector 218 may be configured to move or transition between a collapsed state (FIG. 2A), e.g., for advancing the end effector 218 through an outer sheath and into a body cavity for placement adjacent a target tissue, and an expanded state (FIG. 2B), e.g., for capturing the target tissue.

The end effector 218 may have a distal end 222, and may be coupled to an extraction tool 210 using any suitable techniques or may form an integral part of the extraction tool 210. The end effector 218 may have a substantially conical shape, e.g., having an increased diameter at its distal end 222 as shown in FIGS. 2A-2B. The increased diameter may provide a larger opening for capturing and/or retrieving tissue of various dimensions, including relatively large pieces of tissue. In some embodiments, the distal end 222 may be angled proximally, for example, to create a larger cross-sectional area in the opening of the distal end 222 to allow for passage of relatively larger tissue pieces and/or to access under the tissue pieces, somewhat like a scoop. Angling the opening may further assist in the collapse of the distal end 222 when situated within an outer sheath 202.

FIG. 2A, for example, shows the end effector 218 in a collapsed state, such as when enclosed within an outer sheath 202, and FIG. 2B shows the end effector 218 in an expanded state, e.g., upon extending beyond a distal end of the sheath 202 wherein the end effector 218 may expand to full size to grasp tissue. While FIGS. 2A-2B illustrate end effector 218 having a conical shape, other suitable configurations may also be utilized. Further, while sheath 202 may function substantially similar to sheath 102 of FIG. 1, a separate component of the medical device 100, in some embodiments, sheath 202 may form a part of the extraction tool 210, e.g., in addition to a second sheath 102 configured for insertion into a body cavity for introduction of the extraction tool 210.

Figure 3A:
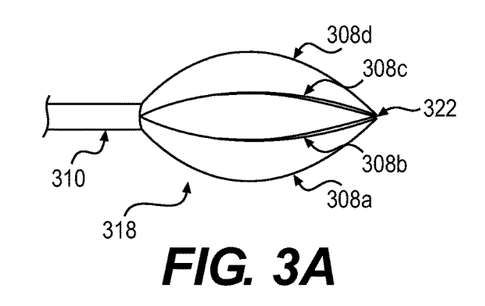
FIGS. 3A and 3B show exemplary end effectors, in accordance with additional embodiments of the present disclosure.
Figure 3B:
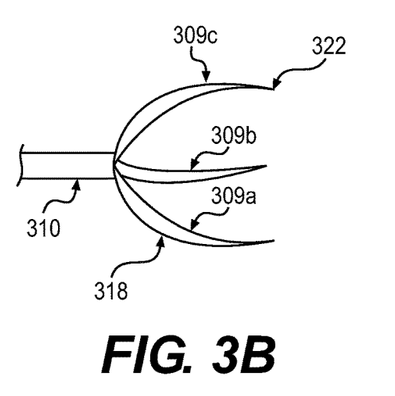

FIGS. 3A and 3B show other exemplary end effectors 318 of extraction tool 310, which may be substantially similar to end effector 118 and extraction tool 110 of FIG. 1, and may include any of the features associated with extraction tool 110. The end effector 318 may include a plurality of legs, e.g., having a basket-like or grasping configuration as illustrated in FIGS. 3A and 3B, respectively. FIG. 3A shows an end effector 318 including a distal end 322, and a plurality of legs 308a, 308b, 308c, 308d (collectively 308) extending to the distal end 322. In some embodiments, the legs 308 may expand in a spiral configuration about the longitudinal axis of the end effector 318, or may expand in a substantially linear configuration about the longitudinal axis of the end effector 318. FIG. 3A shows the end effector 318 with four legs, but other embodiments may include more or fewer legs.

In general, the end effector 318 may be configured to move between a collapsed state and an expanded state. In some embodiments, the end effector 318 may include a plurality of legs 308 that permanently or temporarily join at the distal end 322 of the end effector 318. For example, legs 308 of FIG. 3A may meet at the distal end 322 of the end effector 318 and be permanently connected such that in the collapsed state, the legs 308a, 308b, 308c, and 308d are positioned close to one another and in the expanded state, the legs are expanded radially outward from one another. Thus, in the expanded state, the end effector 318 may capture tissue via spaces between legs 308a, 308b, 308c, and/or 308d. The end effector 318 may then transition to the collapsed state for trapping and/or securing tissue within a cage formed by the legs 308. The transition between the collapsed state and expanded state may be achieved via any suitable mechanism, including deployment via a proximal actuator (not shown). [BSC has a number of commercially available baskets as well as corresponding IP that could be used as examples. Is this helpful?]

With reference to FIG. 3B, the end effector 318 may include a grasper having a plurality of legs 309a, 309b, 309c (collectively 309). While FIG. 3B shows an embodiment having three legs 309, it is understood that fewer than three legs, e.g., two legs, or more than three legs, e.g., four, five, or more, may also be used. The legs 309 may be comprised of a filamentous material such as a wire. Such filamentous material may have any type of cross-sectional shape useful for operating the end effector 318 and securing tissue, for example, round, flat, D-Shaped, square, triangular, and the like. As shown, the legs 309 may be curved, but in other embodiments, the legs 309 may be substantially straight. The end effector 318 may be configured such that the legs 309 move away from and toward one another. For example, the legs may temporarily join at the distal end 322 of the end effector 318 in a collapsed state and expand away from one another in an expanded state. FIG. 3B shows the end effector 318 in the expanded state, where the legs 309 may be extended radially outward from one another, e.g., beyond the distal end of a sheath such as sheath 102 as illustrated in FIG. 1. The transition between the collapsed state and expanded state may be achieved via any suitable mechanism, including deployment via a proximal actuator (not shown). In some embodiments, the end effector 318 may be self-expanding, wherein the legs 309 may be biased radially outward from one another. For example, the legs 309 may be compressed together when enclosed within an outer sheath (e.g., sheath 202 of FIG. 2) and may expand radially outward when the legs 309 are extended beyond the distal end of the outer sheath.

In some embodiments, an inner surface of one or more of the legs 308, 309 may be textured so as to enhance friction against a material and facilitate capture of the material. The legs 308, 309 may include a rough surface, for example, provided by serrations, teeth, etching, or characteristic of the material forming the legs 308, 309. Additionally or alternatively, the legs 308, 309 may include a friction coating, such as a coating comprising an elastomer or other polymer or frictional material, to assist in engaging with, e.g., gripping, tissue.

Each of the legs 308, 309 may have substantially the same shape, or one or more of the legs 308, 309 may have a different shape or configuration with respect to another leg. In some embodiments, the legs 308, 309 may include a flexible material and/or may include one or more suitable rigid materials such as, e.g., metal, metal alloy, polymer, or fiber. The dimensions of the legs may vary. In some embodiments, for example, one or more legs 308, 309 may include a wire material providing for a relatively narrow or thin width. The legs 308, 309 may include a material such as netting, webbing, fabric, or the like between two or more legs 308, 309 to create a net-like basket. In such embodiments, the end effector 318 may be better able to capture relatively smaller pieces of tissue than just the legs 308, 309 alone.

End effectors, e.g., 118, 218, and 318, according to the present disclosure may be provided in any shape or configuration for enhancing or optimizing desired characteristics such as flexibility, rigidity, ease of material capture, and ease of material release, etc. It is understood that the end effector is not limited to the examples provided in FIG. 1, 2A, 2B, 3A, or 3B, but may include other types of end effectors such as, e.g., snare loops, pincers, or forceps, and other structures adapted to capture a material.

Referring again to FIG. 1, the handle 116 may be ergonomically designed to allow the operator to easily hold and control the extraction tool 110. In some embodiments, the handle 116 may include one or more operational elements or control mechanisms to control or actuate the end effector 118, e.g., to move the end effector 118 between a collapsed state and expanded state. In some embodiments, the handle 116 may include one or more operational elements to control one or more optical devices 128. For example, the handle 116 may include one or more control mechanisms, e.g., comprising switches, knobs, gears, sliding buttons, or the like, for controlling an optical device 128 and/or the end effector 118. The handle may be moved proximally and distally to control the location of the end effector 118 with respect to the sheath 102, e.g., to advance and withdraw the end effector 118 through the urethra or other body cavity.

In some embodiments, the handle 116 may include any suitable structure or features for receiving one or more components of the optical device 128, e.g., eyepiece 130 shown in FIG. 1 or other component such as a telescope, fiber optic cable, display screen, or electronic camera. The handle 116 may include one or more ports to introduce an optical device 128 or other medical device into the channel 113 of the extraction tool 110. Vacuum pumps or external fluid systems may be coupled to the extraction tool, e.g., via a port of the handle 116, to generate a suction force at the distal end 114 of the extraction tool 110, or to deliver fluid to the desired location within the patient's body.

The handle 116 may be temporarily or permanently coupled to the proximal end 112 of the extraction tool 110 via any suitable means such as, e.g., an adhesive, welding, or other attachment, or may be integrally formed with the extraction tool 110. The handle 116 may be constructed from any suitable materials such as one or more metals, polymers, ceramic materials, or combinations thereof. In some embodiments, the handle 116 may include a polymeric grip coating to facilitate handling.

The sheath 102 and/or the extraction tool 110 each may comprise one or more suitable biocompatible materials, including rigid, flexible, and/or semi-rigid materials. Exemplary materials include, but are not limited to, polymers, metals and metal alloys, rubber, silicone, and metal-polymer composites. Additionally, the sheath 102 and the extraction tool 110 may be made from the same material(s) or from different material(s). In some embodiments, the sheath 102 may have variable stiffness at different locations around and/or along the sheath 102. The sheath may be reinforced, for example, with braided filaments layered within the wall of the sheath 102, or with reinforcing fibers interspersed within the wall.

The sheath 102 and the extraction tool 110 may include one or more coatings. For example, suitable low-friction material, such as polytetrafluoroethylene (PTFE), polyetheretherketone (PEEK), polyimide, nylon, polyethylene, or other lubricious polymer coatings may be applied to one or more components of the extraction tool 110, the shaft of the extraction tool 110 and/or the end effector 118. For example, one or more lubricious coatings may be applied to facilitate insertion of the sheath 102 and/or extraction tool 110 into the body.

Figure 4:
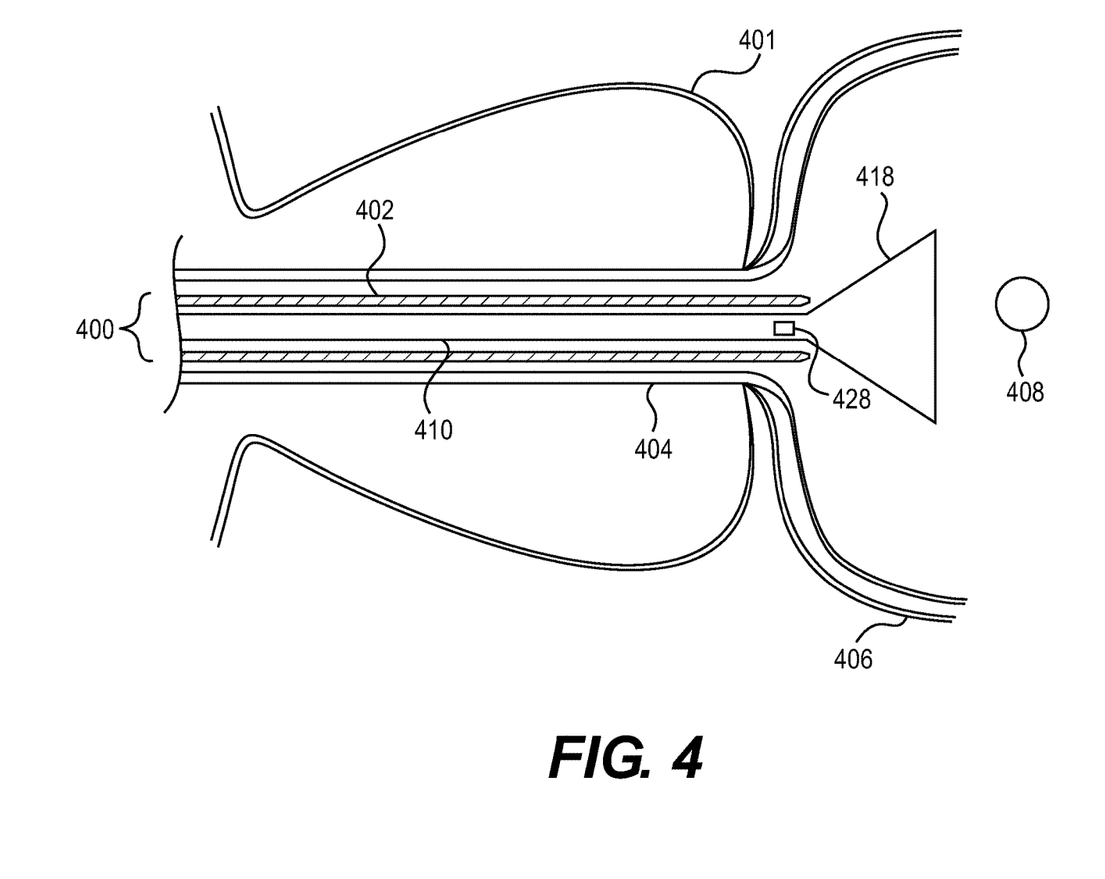
FIG. 4 illustrates an exemplary medical device in a patient's body, in accordance with an embodiment of the present disclosure.

FIG. 4 illustrates an exemplary medical device 400 inserted into the urethra 404 of a patient's body, in proximity to the prostate 401 and the bladder 406. Specifically, FIG. 4 illustrates medical device 400 positioned for removal of tissue 408 located in the bladder 406 following a HoLEP procedure.

The medical device 400 includes a sheath 402 and an extraction tool 410, and may be introduced through the urethra 404 and advanced toward the bladder 406. The extraction tool 410 may include an optical device 428 to enable an operator of the medical device 400 to view excised tissue 408 in the bladder 406. During operation, the end effector 418 may be deployed from a collapsed state to an expanded state, wherein in the expanded state, the excised tissue 408 may be grasped with the end effector 418. Then, the end effector 418 may be moved back into the collapsed state, which may secure the tissue 408 captured within the end effector 418. Thereafter, the operator may proximally pull the extraction tool 410 through the sheath 402 such that the extraction tool 410 with the excised tissue 408 may be removed from the body. The end effector 418 may allow the operator to remove the excised tissue 408 from the body without morcellating the excised tissue 408, e.g., providing for faster removal of tissue. Finally, the operator may retract the sheath 402 from the patient's body.

Figure 5:
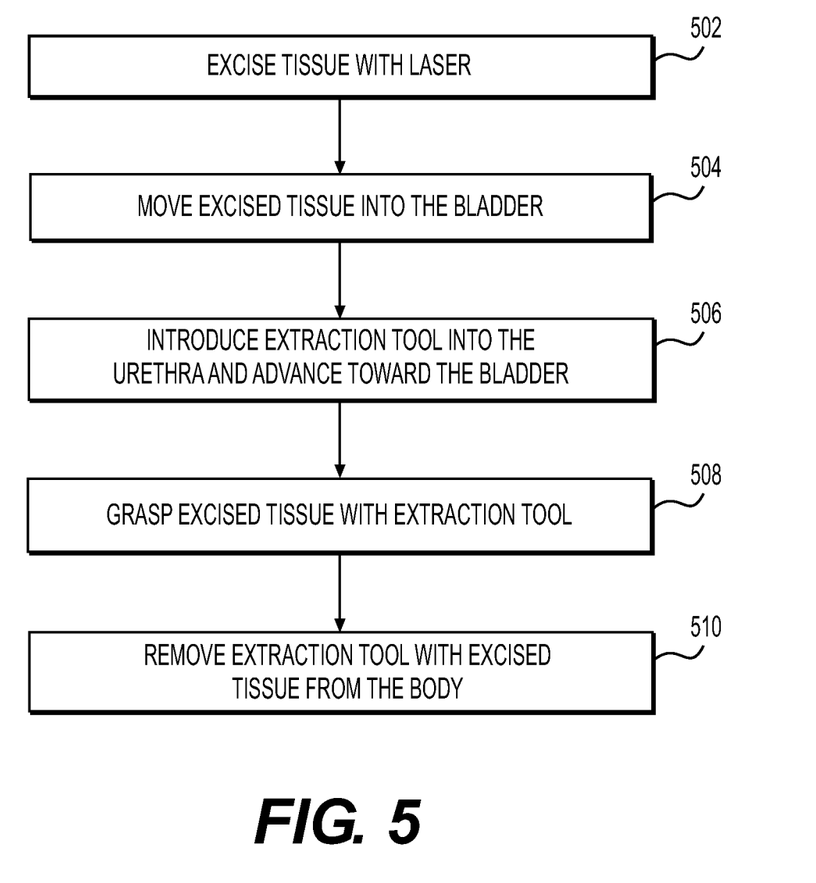
FIG. 5 illustrates an exemplary method, in accordance with an embodiment of the present disclosure.

FIG. 5 illustrates an exemplary method for removing excised tissue from a body according to the present disclosure. The method may be utilized for removing the excised tissue from a patient's bladder as illustrated in FIG. 4, however, it is understood that the method may be utilized for other body organs, for example a uterus or a stomach. In step 502, tissue may be excised with a laser device or apparatus. With reference to FIG. 4, an operator may initially insert a sheath 402 through the urethra 404 and then introduce a laser device or apparatus to excise prostate tissue from the body. In some embodiments a sheath 402 may not be necessary.

Then in step 504, the excised tissue 408 may be moved into the bladder 406. For example, a fluid may be flushed through the sheath 402 and into the urethra 404 to push the excised tissue 408 into the bladder 406. Further, for example, a portion of the sheath 402 may be used to move the excised tissue 408 into the bladder 406. In step 506, the extraction tool 410 may be introduced into the urethra 404 and advanced toward the bladder 406 such that the end effector 418 of the extraction tool 410 may be deployed from a collapsed state to an expanded state.

In step 508, the excised tissue 408 may be grasped or otherwise captured with the extraction tool 410. Specifically, the excised tissue 408 may be grasped with the end effector 418 in the expanded state. After grasping, the end effector 418 may be moved from the expanded state to the collapsed state such that the excised tissue 408 may be secured within the end effector 418. Finally, in step 510, the extraction tool 410 with the excised tissue 408 may be removed from the body without morcellating the excised tissue.

The devices and methods discussed above may provide the capability of removing relatively large pieces of tissue intact, without the need to cut the tissue into smaller pieces. The device and methods disclosed herein thus may reduce the amount of time required to remove the tissue from the body. Embodiments of the present disclosure may be used in various other medical or non-medical procedures, including medical procedures where removal of material from the body is desirable or required. Any aspects of the aforementioned embodiments may be combined with other aspects of the embodiments, or removed, without departing from the scope of the disclosure.

While the embodiments described above are generally directed to a tissue extractor, the present disclosure is not so limited and may be applicable to other medical devices. Any feature discussed and/or shown in connection to one figure or embodiment may be used with any other figure or embodiment.

Moreover, while specific embodiments may have been illustrated and described collectively herein, it should be appreciated that any subsequent arrangement designed to achieve the same or similar purpose may be substituted for the specific embodiments described and shown herein. This disclosure is intended to cover any and all subsequent adaptations or variations of various embodiments. Combinations of the above embodiments, and other embodiments not specifically described herein, will be apparent to those of skill in the art upon reviewing the description.

It is intended that the specification and examples be considered as exemplary only, and departure in form and detail may be made without departing from the scope and spirit of the present disclosure as defined by the following claims.

What is claimed is:

1. A method of removing tissue from a body, the method comprising:
   introducing an extraction tool into a urethra, the extraction tool extending between a proximal end and a distal end, wherein the distal end includes an expandable end effector that forms an at least partially conical shape with a solid circumferential wall in an expanded state, and wherein the extraction tool includes a central channel with an interior diameter greater than about 20 Fr;
   grasping the tissue with the end effector to enclose the tissue within the expandable end effector in the expanded state such that the tissue is surrounded by the solid circumferential wall of the end effector; and
   without morcellating the tissue, removing the extraction tool from the body with the tissue enclosed.

2. The method of claim 1, wherein the extraction tool includes an optical device, wherein at least a portion of the optical device is integrated into the distal end of the extraction tool, and wherein the method further comprises viewing the tissue with the optical device.

3. The method of claim 2, wherein the optical device includes an eyepiece operably connected to a remote imaging system.

4. The method of claim 1, wherein grasping the tissue includes deploying the end effector from a collapsed state into the expanded state, and grasping the tissue with the end effector in the expanded state.

5. The method of claim 4, wherein the end effector is self-expanding.

6. The method of claim 4, wherein the extraction tool includes a handle and, wherein the handle is movable proximally or distally to control a position of the end effector within the body.

7. The method of claim 1, wherein an inner surface of the end effector includes a texture for grasping the tissue, and wherein an outer surface of the end effector includes a hydrophilic material or coating.

8. The method of claim 1, further comprising securing the tissue with the end effector after grasping.

9. The method of claim 1, wherein the tissue includes prostate tissue.

10. The method of claim 1, wherein the tissue includes loose tissue located in a bladder.

11. The method of claim 1, further comprising an initial step of introducing a sheath into the urethra, and then introducing the extraction tool into the sheath.

12. The method of claim 11, wherein pulling the extraction tool proximally through the sheath for removal secures the tissue within the extraction tool.

13. The method of claim 11, wherein the sheath includes an inlet for introducing a fluid into the sheath.

14. The method of claim 13, further comprising introducing a saline solution into the sheath through the inlet.

15. The method of claim 1, wherein the central channel includes an interior diameter greater than about 26 Fr.

16. A method of performing holmium laser enucleation of the prostate, the method comprising:
   excising prostate tissue with a laser apparatus;
   moving the excised tissue into a bladder;
   introducing an extraction tool into a urethra and advancing the extraction tool toward the bladder, the extraction tool extending between a proximal end and a distal end, wherein the distal end includes an expandable end effector that forms an at least partially conical shape with a solid circumferential wall in an expanded state, and wherein the extraction tool includes a channel with an interior diameter greater than about 26 Fr;
   grasping the excised tissue with the end effector to enclose the tissue within the expandable end effector in the expanded state such that the tissue is surrounded by the solid circumferential wall of the end effector; and
   removing the extraction tool from the body with the excised tissue enclosed without morcellating the tissue.

17. The method of claim 16, wherein the extraction tool includes an optical device, wherein at least a portion of the optical device is integrated into the distal end of the extraction tool, and wherein the method further comprises viewing the excised tissue with the optical device.

18. The method of claim 16, wherein grasping the excised tissue includes deploying the end effector from a collapsed state into the expanded state, and grasping the excised tissue with the end effector when in the expanded state.

19. The method of claim 16, wherein the channel includes an interior diameter between about 26 Fr and about 27 Fr.

* * * * *